US010386384B2

(12) United States Patent
Hong et al.

(10) Patent No.: US 10,386,384 B2
(45) Date of Patent: Aug. 20, 2019

(54) SYSTEM AND METHOD FOR DIGITAL INLINE HOLOGRAPHY

(71) Applicant: REGENTS OF THE UNIVERSITY OF MINNESOTA, Minneapolis, MN (US)

(72) Inventors: Jiarong Hong, New Brighton, MN (US); Mostafa Toloui, Minneapolis, MN (US)

(73) Assignee: REGENTS OF THE UNIVESITY OF MINNESOTA, Minneaopolis, MN (US)

( * ) Notice: Subject to any disclaimer, the term of this patent is extended or adjusted under 35 U.S.C. 154(b) by 367 days.

(21) Appl. No.: 15/422,021

(22) Filed: Feb. 1, 2017

(65) Prior Publication Data
US 2017/0219998 A1    Aug. 3, 2017

Related U.S. Application Data

(60) Provisional application No. 62/289,669, filed on Feb. 1, 2016.

(51) Int. Cl.
G01P 5/26         (2006.01)
G03H 1/00         (2006.01)
(Continued)

(52) U.S. Cl.
CPC ............ *G01P 5/26* (2013.01); *G01N 15/0227* (2013.01); *G03H 1/0443* (2013.01);
(Continued)

(58) Field of Classification Search
CPC .... G01P 5/26; G01N 15/0227; G03H 1/0443; G03H 1/0866; G03H 2001/0033;
(Continued)

(56) References Cited

U.S. PATENT DOCUMENTS 4,572,667 A * 2/1986 Rogers ...................... G01P 5/26
                                                              250/461.1
5,532,814 A    7/1996 Cha
(Continued)

FOREIGN PATENT DOCUMENTS

EP    0436125 A1    11/1990

OTHER PUBLICATIONS

R.J. Adrian et al.,"Particle Image Velocimetry", No. 30. Cambridge University Press, 2011, Figure 2.5, 1 pp.
(Continued)

*Primary Examiner* — Eric L Bolda
(74) *Attorney, Agent, or Firm* — Billion & Armitage; Michael A. Collins

(57) ABSTRACT

A method of extracting particles from a two-dimensional (2D) hologram recorded as part of a digital inline holography system includes reconstructing a three-dimensional (3D) optical field from the recorded 2D hologram. In addition, particles are extracted/segmented from the 3D optical field, wherein segmented particles are identified by particle location in three-dimensional space and a cross-sectional area of the segmented particle. Based on the identified particle location and cross-sectional area, extracted particles are removed from the 2D hologram to generate an updated 2D hologram. These steps are repeated iteratively until a threshold is met.

26 Claims, 10 Drawing Sheets

(51) Int. Cl.
- G03H 1/04 (2006.01)
- G03H 1/08 (2006.01)
- G01N 15/00 (2006.01)
- G01N 15/02 (2006.01)

(52) U.S. Cl.
CPC ... G03H 1/0866 (2013.01); *G01N 2015/0046* (2013.01); *G03H 2001/0033* (2013.01); *G03H 2001/0447* (2013.01); *G03H 2001/0883* (2013.01); *G03H 2210/30* (2013.01)

(58) Field of Classification Search
CPC ... G03H 2001/0038; G03H 2001/0447; G03H 2001/0883
See application file for complete search history.

(56) References Cited

U.S. PATENT DOCUMENTS

| | | |
|---|---|---|
| 5,548,419 A | 8/1996 | Adrian et al. |
| 5,905,568 A | 5/1999 | McDowell et al. |
| 6,078,392 A | 6/2000 | Thomas et al. |
| 2014/0220622 A1* | 8/2014 | Twardowski ...... G01N 15/0227 435/39 |

OTHER PUBLICATIONS

R.J. Adrian, "Twenty years of particle image velocimetry", Experiments in Fluids, Jul. 6, 2005, 11 pp.

D.A. Agard,"Optical Sectioning Microscopy: Cellular Architecture in Three Dimensions", Annual review of biophysics and bioengineering, 13, 191-219 (1984).

L. Ahrenberg et al. "Using commodity graphics hardware for real-time digital hologram view-reconstruction," Display Technology, Journal 5, 4, 111-119 (2009).

Barnhart et al., "Phase-Conjugate Holographic System for High-Resolution Particle-Image Velocimetry", Applied Optics 33(3), Oct. 1994, 7159-7179.

J. Burns et al.,"Data Extraction from Underwater Holograms of Marine Organisms", in Oceans 2007—Europe (IEEE), pp. 1-6 (2007).

Elsinga, "Complete removal of ghost particles in Tomographic-PIV", G.E. Elsinga, "Complete removal of ghost particles in Tomographic-PIV", in 10th International Symposium on Particle Image Velocimetry (KSOV, 2013), pp. 103.

Cheong et al. "Strategies for three-dimensional particle tracking with holographic video microscopy", Optics express, 18 (13): 13563-13573 (2010).

Fugal et al., "Cloud particle size distributions measured with an airborne digital in-line holographic instrument", Atmospheric Measurement Techniques, 2(1), 259-271 (2009).

G.E. Elsinga et al., "Tomographic particle image velocimetry", Experiments in Fluids, 41(6): 933-947 (2006).

J. Gao, "Development and applications of digital holography to particle field measurement and in vivo biological imaging", PHD dissertation, Purdue University (2014).

S. Ghaemi et al., "Turbulent structure of high-amplitude pressure peaks within the turbulent boundary layer", Journal of Fluid Mechanics, 735, 381-426. (2013).

Gire et al.,"Digital Holography of particles: benefits of the "inverse problem" approach", Measurement Science and Technology, 19(7), 074005 (2008).

Goodman, "Introduction to Fourier Optics", Joseph W. Goodman. "Introduction to Fourier Optics", McGraw-Hill (1968).

J. Graham et al., "A Web Services-accessible database of turbulent channel flow and its use for testing a new integral wall model for LES", Journal of Turbulence (2015)—(under review).

Gray, et al., "A processing system for the analysis of particle displacement holograms" SPIE vol. 2005, 1993, 636-647.

D.R. Guildenbecher et al., "Digital holography reconstruction algorithms to estimate the morphology and depth of nonspherical absorbing particles", in SPIE Optical Engineering Applications International Society for Optics and Photonics (2012).

Hart, Douglas P., "High-Speed PIV Analysis Using Compressed Image Correlation", Journal of Fluids Engineering 120, Sep. 1998, pp. 463-470.

T. Hori et al., "High-speed scanning stereoscopic PIV for 3D vorticity measurement in liquids", Measure Science and Technology, 15(6):1067 (2004).

Ichihashi, Yasuyuki et al. "Real-time capture and reconstruction system with multiple GPUs for a 3D live scene by a generation from 4K IP images to 8K holograms", Optics Express, 20 (10):21645-21655 (2012).

Jiarong Hong et al., "Algal Toxins Alter Copepod Feeding Behavior", PloS one, 7(5) (2012).

John C. Crocker et al., "Methods of Digital Video Microscopy for Colloidal Studies", Journal of colloid and interface science 1279 (1): 298-310 (1996).

Joseph Katz et al., "Applications of Holography in Fluid Mechanics and Particle Dynamics", Annual Review of Fluid Mechanics, 42:531-555 (2010).

Wing Lai et al., "Volumetric Three-Component Velocimetry: a New Tool for 3D Flow Measurement", In Proceedings of 14th international symposium on applications of laser techniques to fluid mechanics. Lisbon, Portugal (2008).

Latychevskaia et al., "Depth-resolved holographic reconstructions by three-dimensional deconvolution", Optic express 18, No. 21 (2010), 22527-22544.

T. Latychevskaia et al., "Holographic time-resolved particle tracking by means of three-dimensional volumetric deconvolution", Optic Press, 22(17):2094-21003 (2014).

Yi Li et al., "A public turbulence database cluster and applications to study Lagrangian evolution of velocity increments in turbulence", Journal of Turbulence, 9(31) (2008).

Lisa Dixon et al., "Holographic deconvolution microscopy for high-resolution particle tracking", Optic Express, 19(17): 16410-16417 (2011).

Lozano, A et al., "Use of Holography in Particle Image Velocimetry Measurements of a Swirling Flow", Experiments in Fluids 27, 1999, pp. 251-261.

Malek, et al., "Digital in-line holography: influence of the shadow density on particle field extraction", Optic Express, 12(10): 2270-2279 (2004).

H. Meng et al., "Holographic particle image velocimetry: from film to digital recording", Meas. Sci. Technology, 15(4), 673-685 (2004).

Hui Meng et al., "Intrinsic speckle noise in in-line particle holography", Optical Society of America A, 10:2046-2058 (1993).

M. N. Rahman et al., "Effect of particle concentration and turbidity on particle characterization using digital holography", Chemical Engineering Research and Design, 92(2), 24-255 (2014).

Orzo, et al., "GPU implementation of volume reconstruction and object detection in digital holographic microscopy", In Cellular Nanoscale Networks and Their Applications (CNNA), 2010 12th International Workshop on, pp. 1-4, IEEE (2010).

Pan, et al., "Digital holography of particle fields: reconstruction by use of complex amplitude", G. Pan et al., "Digital holography of particle fields: reconstruction by use of complex amplitude", Applied Optics, 42(5):827-833 (2003).

Pereira, et al., "Two-frame 3D particle tracking", Pereira et al., "Two-frame 3D particle tracking", Measurement Science and Technology, 17(7), 160 (2006).

Royer, "An Application of high-speed microholography: the metrology of fogs", H. Royer et al., "An Application of high-speed microholography: the metrology of fogs", Nouv. Rev. Optique, 5(20), 87-93 (1974) 1974.

Sarder, et al., "Deconvolution Methods for 3-D Fluorescence Microscopy Images", Pinaki Sander et al., "Deconvolution Methods for 3-D Fluorescence Microscopy Images", Singal Processing Magazine, IEEE 23(3):32-45 (2006).

Schanz et al., "'Shake the Box': a highly efficient and accurate Tomographic Particle Tracking Velocimetry (TOMO-PTV) method using prediction of particle positions", In PIV13, 10th International Symposium on Particle Image Velocimetry, Netherlands (2013).

(56) References Cited

OTHER PUBLICATIONS

J. Sheng et al., "Buffer layer structures associated with extreme wall stress events in a smooth wall turbulent boundary layer", Journal of Fluid Mechanics 633:17-60 (2009).

J. Sheng et al., "Digital holographic microscope for measuring three-dimensional particle distributions and motions", Applied Optics, 45(16):3893-3901 (2006).

J. Sheng et al., "Using digital holographic microscopy for simultaneous measurements of 3D near wall velocity and wall shear stress in a turbulent boundary layer", Experiments in fluids, 45(6):1023-1035 (2008).

Tomoyoshi Shimobaba et al., "Real-time digital holographic microscopy using the graphic processing unit", Optic Express, 16(16):11776-11781 (2008).

D. K. Singh et al., "Automatic threshold technique for holographic particle field characterization", Applied Optics, 51(7): 3874-3887 (2012).

D.K Singh et al., "Three-dimensional investigation of liquid slug Taylor flow inside a micro-capillary using holographic velocimetry", Experiments in Fluids, 56(1), 1-15 (2015).

F. Slimani et al., "Near-field Lorenz-Mie theory and its application to microhologmphy", Applied Optics, 23(22), 4140-4148 (1984).

Soulez et al., "Inverse problem approach for particle digital holography: accurate location based on local optimisation", Optical Society of America A, 24(4): 1164-1171 (2007).

Siddharth Talapatra et al., "Three-dimensional velocity measurements in a roughness sublayer using microscopic digital in-line holography and optical index matching", Measurement Science and Technology, 24(2):024004 (2013).

Tanaka et al., "Reduction of reconstructed particle elongation using iterative min-max filtering in holographic particle image velocimetry", 17th International Symposium on Applications of Laser Techniques to Fluid Mechanics. Lisbon, Portugal. (2014).

Tian et al., "Quantitative measurement of size and three-dimensional position of fast-moving bubbles in air-water mixture flows using digital holograpy", Applied optics 49 (9): 1549-1554 (2010).

C.E. Wilert et al., "Three-dimensional particle imaging with a single camera", Exp. Fluids 12(6), 353-358 (1992).

Yang, Weidong et al., "Depth-of-focus reduction for digital in-line holography of particle fields", Optic Letters, 30(11):1303-1305 (2005) 6 pp.

Zhang et al., "Turbulent flow measurement in a square duct with hybrid holographic PIV", Experiments in Fluids 23, 1997, pp. 373-381.

Y. Zhang et al., "Influence of some recording parameters on digital holographic particle image velocimetiy", Opt. Eng. 45(7), 075801 (2006), 10 pp.

\* cited by examiner

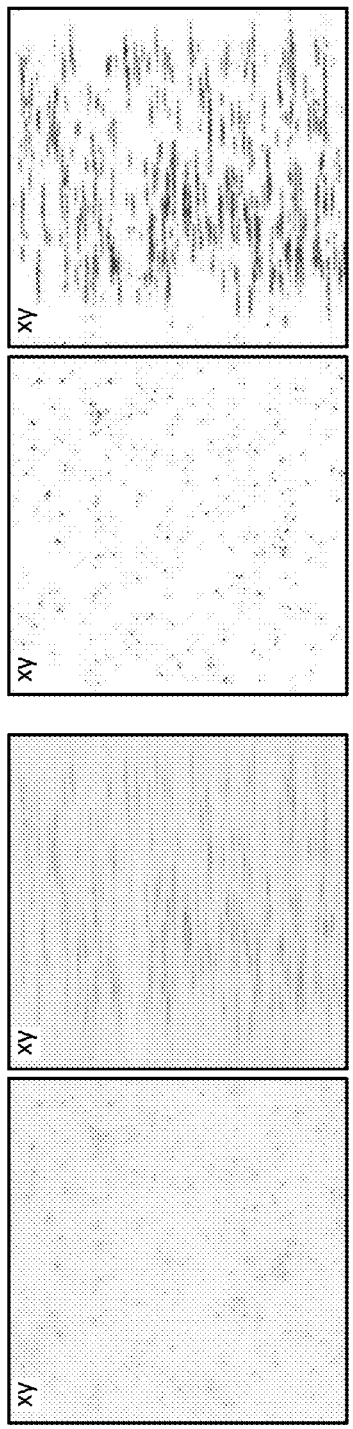
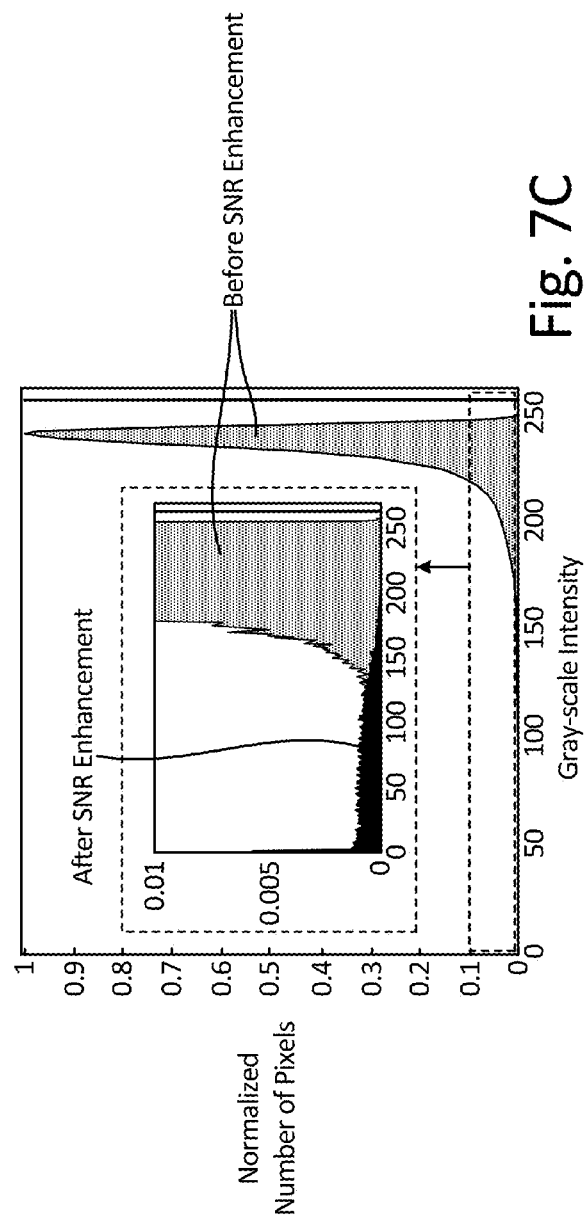
Fig. 7A
Fig. 7B
Fig. 7C

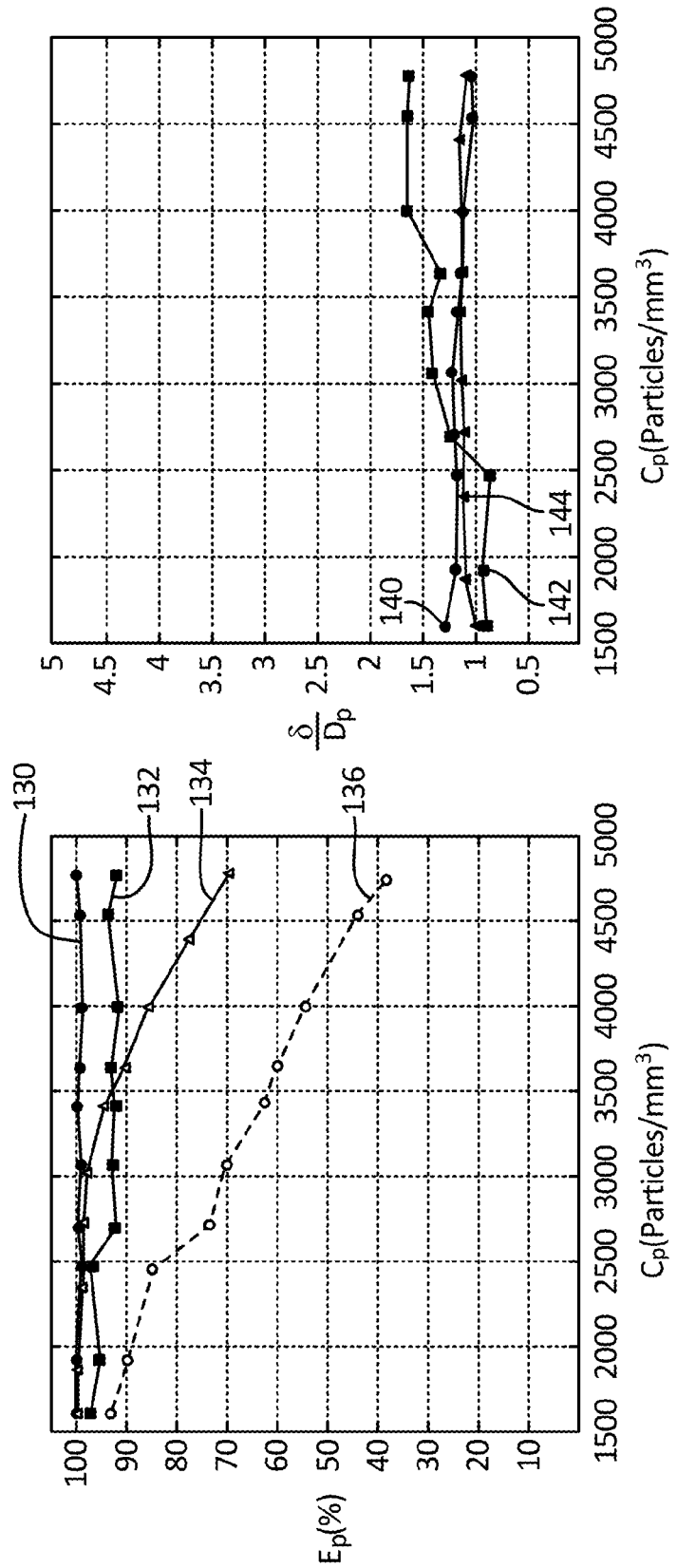

SYSTEM AND METHOD FOR DIGITAL INLINE HOLOGRAPHY

TECHNICAL FIELD

The present disclosure is related generally to digital inline holography (DM) systems and methods, and in particular to using DM systems and methods for particle image velocimetry applications (DIH-PIV).

BACKGROUND

Particle image velocimetry (PIV) is utilized to understand the flow dynamics of a fluid. In general, PIV involves "seeding" the fluid with tracer particles that can be imaged and tracked. The motion of the tracer particles is used to calculate flow dynamics of the flow being studied. In order for the tracer particles to faithfully represent the path of the fluid, the tracer particles must be sufficiently small. In addition, a higher concentration of the tracer particles provides more information regarding the flow dynamics of the fluid, and is therefore beneficial. However, as the size of the tracer particles becomes sufficiently small, and the concentration increases it becomes more difficult to image the tracer particles, particularly in three-dimensional space.

Digital inline holography (DIH) is one solution for imaging particles in PIV applications. DIH is different from most imaging techniques in that it relies on illuminating the tracer particles with coherent light from a single-beam source, and then records the interference pattern between the scattered and undisturbed portions of the beam. The information is recorded in the form of a two-dimensional image comprised of patterns resulting from the interference (some destructive, some constructive) between the scattered light and unscattered light, but retains three-dimensional information regarding the particles imaged. This encoded information, known as a hologram, can then be used to reconstruct the shape and position of the particles that caused the scattering of light. In this way, DIH can be utilized in PIV applications to image the tracer particles in a fluid.

However, DIH-PIV suffers from several drawbacks. For example, DIH-PIV suffers from poor longitudinal resolution (i.e., in the direction of coherent light source). As a result, uncertainty is introduced with respect to longitudinal velocity measurements. In addition, extracting/reconstructing 3D tracer information from the 2D hologram requires sophisticated image processing that relies on tuning parameters that often-times rely on user interaction. As such, optimal selection of these parameters is highly dependent on the judgment and experience of the user/technician. Finally, as the tracer particle concentration increases, the noise generated from the cross-interference among adjacent particles increases, which significantly lowers the signal-to-noise ratio (SNR) of the holograms. As a result, DIH-PIV must operate with low concentrations of particle tracers, which limits the spatial resolution of the velocity field in PIV applications.

It would therefore be beneficial to develop a DIH-PIV system that overcomes one or more of the above obstacles.

SUMMARY

According to one embodiment, a digital inline holography particle image velocimetry (DIH-PIV) system includes a holographic recording system and a processing system. The holographic recording system is configured to record two-dimensional (2D) holograms in response to interaction of planar wave fronts with a plurality of particles located in a particle field. The processing system receives the recorded 2D holograms and processes the 2D holograms to identify particle locations within the particle field. In particular, the processing system (a) reconstructs a three-dimensional (3D) optical field from the recorded 2D hologram, (b) segments particles from the reconstructed 3D optical field, wherein segmented particles are identified by particle location in three-dimensional space and a cross-sectional area of the segmented particle, and (c) computationally removes the segmented particles from the 2D hologram to generate an updated 2D hologram, wherein the steps (a)-(c) are repeated until a threshold is met.

According to another embodiment, a method of extracting particles from a two-dimensional (2D) hologram recorded as part of a digital inline holography system includes reconstructing a three-dimensional (3D) optical field from the recorded 2D hologram. Particles are identified/segmented within the reconstructed 3D optical field, wherein segmented particles are identified by particle location in three-dimensional space and a cross-sectional area of the segmented particle. The segmented particles are computationally removed from the 2D hologram to generate an updated 2D hologram. These steps are repeated to identify additional particles within the 2D hologram until a threshold has been met.

According to another embodiment, a computer-readable storage medium includes data stored therein representing software executable by one or more processors located in a computer system. Execution of the software by the one or more processors causes the computer system to identify particles within a recorded 2D hologram by performing a method that includes reconstructing a three-dimensional (3D) optical field from the recorded 2D hologram. The method further includes segmenting particles from the reconstructed 3D optical field, wherein segmented particles are identified by particle location in three-dimensional space and a cross-sectional area of the segmented particle. The segmented particles are then computationally removed from the 2D hologram to generate an updated 2D hologram. These steps are repeated until a threshold number of iterations or particles have been removed.

BRIEF DESCRIPTION OF THE DRAWINGS

FIGS. 6a and 6b are visual representations of the 3D optical field created as a result of numerical reconstruction, wherein FIG. 6a illustrates the 3D optical field prior to 3D deconvolution and FIG. 6b illustrates the 3D optical field following 3D deconvolution according to an embodiment of the present invention.

FIG. 7a illustrates the xy and xz plane minimum intensity maps prior to 3D local signal-to-noise (SNR) enhancement; and FIG. 7b illustrates the xy and xz plane minimum intensity maps subsequent to 3D local signal-to-noise (SNR) enhancement to illustrate the effect of applying the 3D local SNR enhancements.

FIG. 7c illustrates a normalized number of pixels charted against gray-scale intensity both before 3D local SNR enhancement and after 3D local SNR enhancement

FIG. 9a is a graph that compares the extraction rate $E_p$ of particles under various operating parameters according to embodiments of the present invention.

FIG. 9b is a graph that compares the positioning error of particles extracted under various operating parameters according to embodiments of the present invention.

DETAILED DESCRIPTION

The present disclosure provides a system and method for digital inline holography (DIH). In particular, the present disclosure is described with respect to particle image velocimetry (PIV) applications, but the DIH systems and methods described may be utilized in other imaging applications as well. For DIH-PIV applications the present disclosure provides a system and method to accurately identify and extract a high percentage of tracer particles even as particle concentration levels increase. In particular, the DIH system and method utilizes an inverse iterative particle extraction (IIPE) process to increase the number of particles that can be identified and extracted from the 2D hologram. Additionally, the present disclosure describes a plurality of enhancements utilized to improve longitudinal resolution and signal-to-noise ratio, which in turn aids in identifying and extracting particles during the IIPE process.

Figure 1:
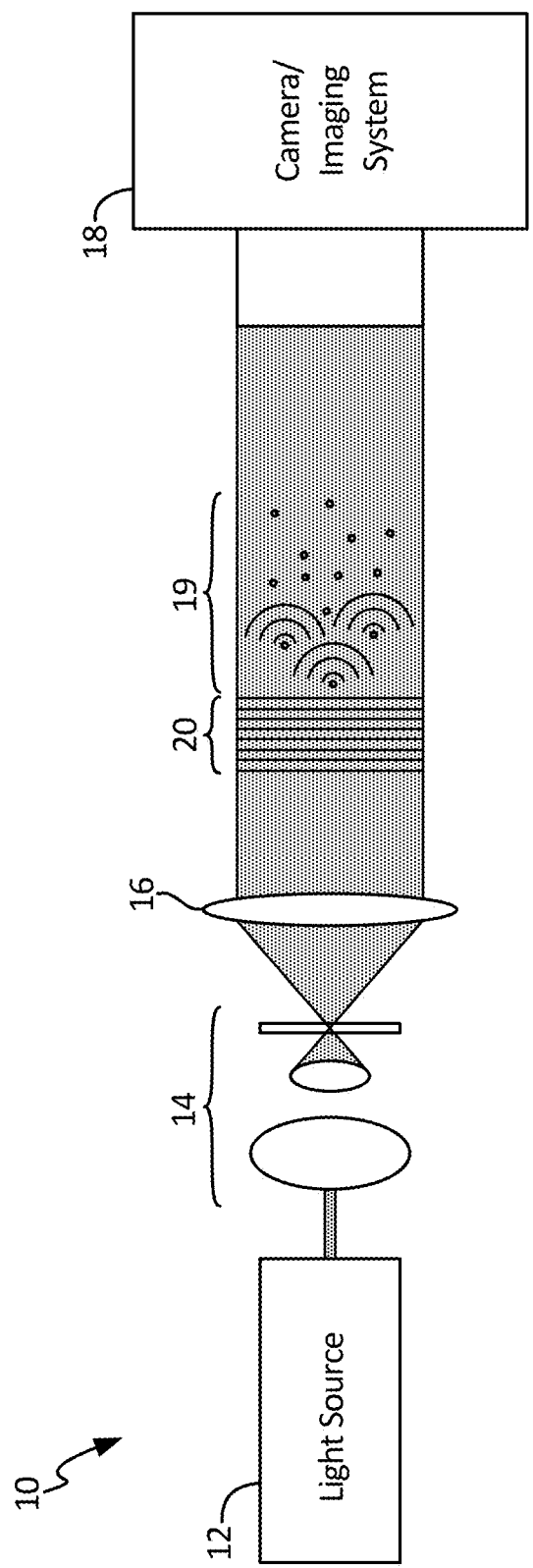
FIG. 1 is a schematic diagram illustrating the optical setup of a digital in-line holography system according to an embodiment of the present invention.

FIG. 1 is a schematic diagram illustrating the optical setup of digital in-line holography (DIH) system 10 according to an embodiment of the present invention. In the embodiment shown in FIG. 1, DIH system 10 includes light source 12 (e.g., laser), spatial filter 14, collimator lens 16 and camera 18 (e.g., charge-coupled device (CCD) for capturing 2D images). In general, light source 12 provides a coherent light source (i.e., light waves emitted have the same frequency and phase). Spatial filter 14 filters or removes aberrations in the light source 12. Collimator lens 16 acts to align the light source into planar wave fronts (20), which are used to illuminate the tracer particles (particle field 19) seeded within the fluid being studied. In particular, the planar wave front 20 interacts with the tracer particles, with tracer particles causing planar wave front 20 to scatter. The scattered and unscattered waves form an interference pattern that is recorded by camera 18, wherein the recorded interference pattern is referred to as a hologram. Although the hologram is stored as a two-dimensional (2D) image, the hologram is subsequently utilized to reconstruct a 3D representation of the tracer particles (discussed in more detail with respect to FIG. 2). That is, in contrast with typical imaging techniques, in which only objects at a given focal distance can be imaged, the 2D hologram contains all necessary information to reconstruct objects in 3D space at any focal plane.

Figure 2:
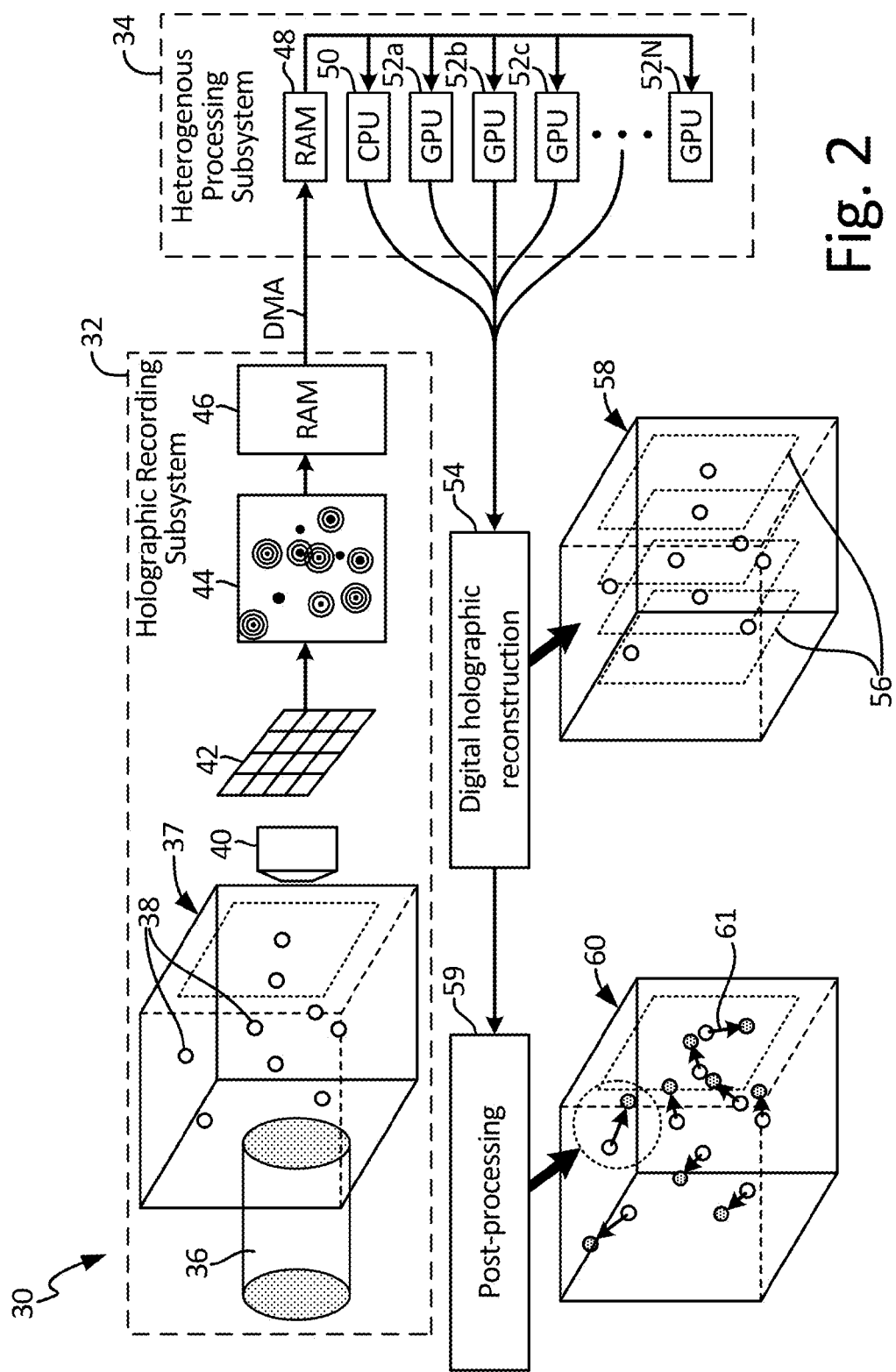
FIG. 2 is a schematic/flowchart diagram that illustrates the holographic recording and processing of holographic images to reconstruct the 3D particle information according to an embodiment of the present invention.

FIG. 2 is a schematic/flowchart diagram that illustrates the use of digital inline holographic (DIH) recording and processing of holographic images to reconstruct the 3D particle information used for particle image velocimetry (PIV) according to an embodiment of the present invention. In particular, DIH-PIV system 30 shown in FIG. 2 is divided into a holographic recording subsystem 32 and heterogeneous processing subsystem 34. Holographic recording subsystem 32, as discussed with respect to FIG. 1, is responsible for illuminating the tracer particles and recording the 2D holograms created by the scattering of light and resulting interference pattern between scattered and unscattered light. Heterogeneous processing subsystem 34 is responsible for reconstructing the tracer particles in three-dimensional space based on the recorded 2D hologram, and providing the object identification/tracking required to determine the velocity of the tracer particles.

Recording subsystem 32 includes laser 36, imaging volume 37 (which is comprised of a plurality of tracer particles or imaging objects 38), lens objective 40, digital sensor or camera 42 utilized to capture 2D holograms 44, and memory device 46. Laser 36 acts as the light source to provide a coherent beam to image objects (e.g., tracer particles 38) located in imaging volume 37. Lens objective 40 and digital sensor 42 included as part of a camera—record the resulting interference caused by the scattering of light interacting with the tracer particles. The resulting 2D hologram 44 is recorded and stored to memory (e.g., random access memory 46).

The stored hologram is provided to heterogeneous processing subsystem 34, which is comprised of memory 48 and one or more processors such as central processing unit 50 and one or more graphical processing units 52. Heterogeneous processing subsystem 34 acts to digitally reconstruct the 3D image (i.e. shape and position) of the tracer particles, which allows for the identification and tracking of the particles required to determine the velocity of the tracer particles. In particular, in the embodiment shown in FIG. 2, the plurality of CPUs 50 and GPUs 52 implement an algorithm to identify object information based on the stored 2D hologram as shown at step 54. For PIV applications, this may include identifying particles 38 within the viewing volume 37, and extracting object information such as location, particle size, etc. In particular, as discussed in more detail below, the digital holographic reconstruction performed at step 54 includes reconstructing a plurality of cross sectional slices 56 (shown below step 54) each located at a different in-focus plane—which together illustrate the location of the plurality of particles in three-dimensional space as shown by the 3D visualization 58 of the reconstructed cross-sectional slices 56. Post-processing at step 60 allows objects (e.g., particles) to be tracked through successive frames of data to allow 3D motion-tracking of objects. In PIV applications this information is used to detect local flow velocities as shown in reconstructed viewing volume 61. In the embodiment shown in FIG. 2, unshaded circles represent particles identified at a first time t1, and shaded circles represent particles identified at a second time t2. The location of the particles at times t1 and t2 can be utilized to determine attributes such as velocity, direction, etc.

Figure 3B:
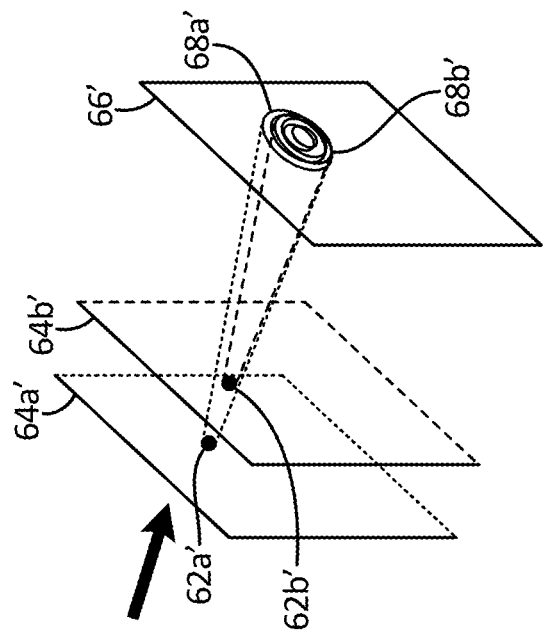
FIGS. 3A and 3B are schematics illustrating the effect of particle placement on hologram creation and the resulting interference created between particles according to an embodiment of the present invention.
Figure 3A:
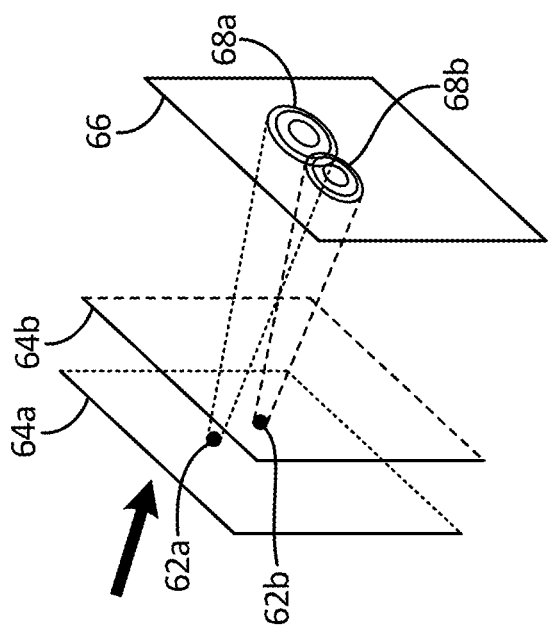

FIG. 3*a* is a schematic diagram that illustrates creation of first and second interference patterns created by first and second particles located at different locations within the viewing volume. FIG. 3*b* is a schematic diagram that illustrates how the location of the particles can result in interference/overlap between the first and second interference patterns, which complicates the reconstruction process.

In particular, FIG. 3*a* illustrates a first particle 62*a* location in a first cross-sectional plane 64*a* and second particle 62*b* located in a second cross-sectional plane 64*b*. The position of first and second particles 62*a* and 62*b* are recorded in 2D hologram 66, wherein the light scattered by particle 62*a* is illustrated by interference pattern 68*a* and the light scattered by particle 62*b* is illustrated by interference pattern 68*b*. Because particle 62*a* is located in a longitudinal plane farther away from the imaging surface of the 2D hologram than particle 62*b*, light scattered by particle 62*a* results in a different interference pattern (e.g. fringe spacing and fringe size) from that caused by the scattering of light associated with particle 62*b*. This example illustrates how the longitudinal position of the particles can be reconstructed from the patterns generated as part of the 2D hologram.

In the example shown in FIG. 3*b*, tracer particle 62*a* is located in the same location within cross-sectional plane 64*a* as shown in FIG. 3A. However, tracer particle 62*b'* is located in a different position within cross-sectional plane 64*b'*. As a result, the light scattered by tracer particles 62*a* and 62*b'* overlaps with one another such that the resulting interference patterns 68*a* and 68*b'* recorded as part of hologram 66' significantly interfere with one another, making it more difficult to reconstruct the positions of the individual tracer particles from the 2D hologram. As the density/concentration of tracer particles increases, the likelihood of significant interference/overlap between the interference patterns increases, making it more and more difficult to reconstruct the location of the particles from the 2D hologram. In particular, the number of particles correctly "extracted" from the 2D hologram is useful in determining how well a particular reconstruction effort operates. For example, in the embodiment shown in FIG. 3*a*, most reconstruction systems/algorithms would successfully identify/extract tracer particles 62*a* and 62*h* from the 2D hologram. However, it is significantly more difficult for a reconstruction system/algorithm to extract tracer particles 62*a* and 62*b'* from the 2D hologram shown in FIG. 3B, due to the interference between the resulting interference patterns 68*a* and 68*b'*. As discussed in more detail with respect to an embodiment of the reconstruction algorithm shown in FIG. 5, the present invention utilizes an iterative approach—specifically, inverse iterative particle extraction technique to identify and extract particles 62*a* and 62*b'*.

Figure 4:
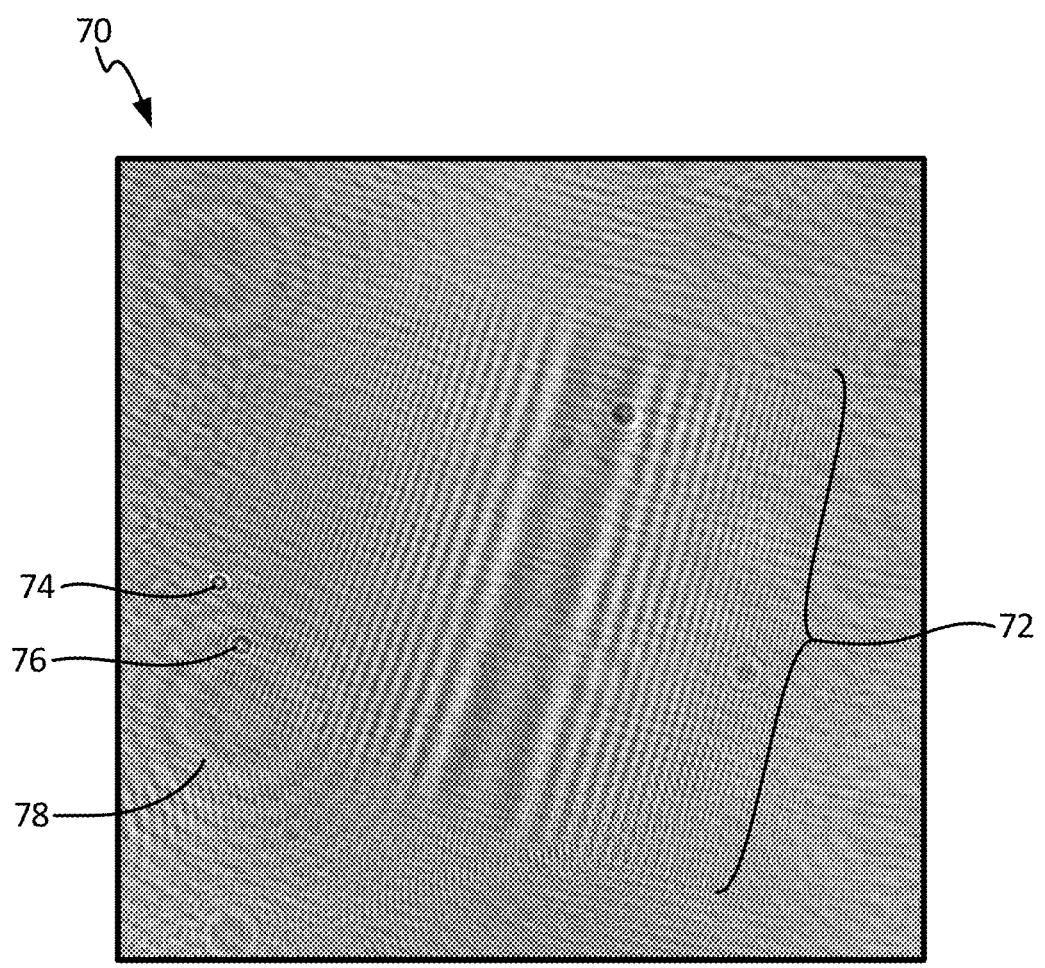
FIG. 4 is a sample holographic image captured according to an embodiment of the present invention.

FIG. 4 is a sample 2D holographic image captured according to an embodiment of the present invention. In particular, the sample hologram 70 shown in FIG. 4 illustrates the resulting interference patterns generated in response to scattered light (from particles/objects) interacting with unscattered light. For example, 2D hologram 70 includes a first interference pattern 72 that results from light scattered in response to a long rod-shaped object, as well as a plurality of interference patterns 74, 76 and 78 generated by particles located at different longitudinal planes within the viewing volume. With respect to the particles highlighted in sample hologram 70, pattern 74 appears smaller, and therefore was created by a particle located closer to the camera imaging surface than the particle resulting in the creation of pattern 78. In this way, particle location can be reconstructed in three-dimensional space. In addition to reconstruction of particle locations, the embodiment shown in FIG. 4 illustrates that various types and shapes of objects can be imaged, not just small particles used as tracers for PIV applications.

Figure 5:
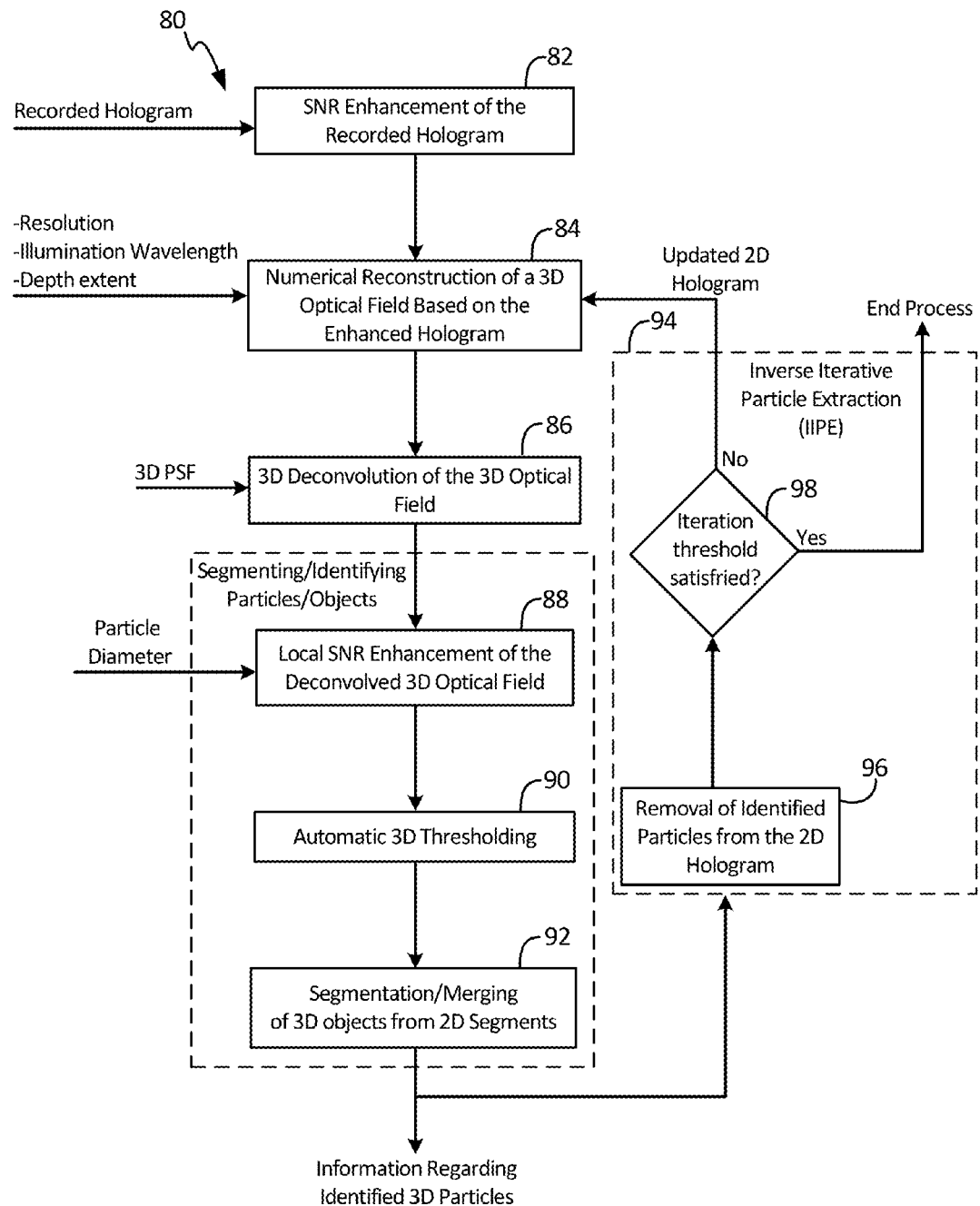
FIG. 5 is a flowchart illustrating the processing of holographic data according to an embodiment of the present invention.

FIG. 5 is a flowchart 80 illustrating the processing of holographic data according to an embodiment of the present invention. As described above with respect to FIGS. 1 and 2, holographic recording subsystem 32—which includes a laser and recording medium—is utilized to image and store a 2D hologram, an example of which was shown with respect to FIG. 4. The 2D hologram (referred to as the "recorded hologram) is provided to heterogeneous processing subsystem 34, which includes one or more processors—including for example, one or more CPUs 50 and GPUs 52, which implement the plurality of steps described with respect to FIG. 5.

At step 82, signal-to-noise (SNR) enhancement is applied to the recorded hologram (raw hologram). In one embodiment, SNR hologram enhancement comprises subtraction of the recorded hologram from corresponding time-averaged holograms followed by gray-scale equalization. Subtraction of the recorded hologram from a time-averaged hologram results in the background (which does not change) being largely removed from the recorded hologram, thereby improving the signal-to-noise ratio of the interference patterns provided in the enhanced hologram. In other embodiments, other well-known enhancement techniques may be utilized to improve the SNR of the recorded hologram.

Figure 6A:
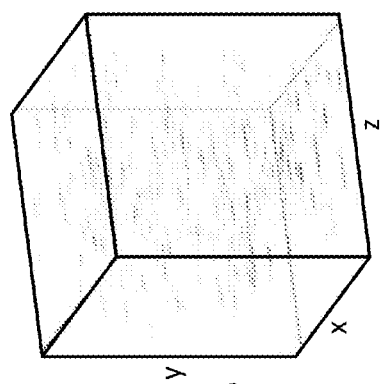

At step 84, the enhanced hologram generated at step 82 is utilized to numerically construct a 3D optical field. The numerical reconstruction provided at step 84 is based on the enhanced hologram generated at step 82 as well as one or more inputs, including resolution, illumination wavelength, and/or depth extent. Based on these inputs, reconstruction involves generating from the enhanced hologram a plurality of 2D images (i.e., slices) that are stacked in the longitudinal direction to create a 3D optical image that defines the location of particles within the 3D viewing volume. The 2D cross-sectional slices are defined by a plurality of pixels, wherein the intensity of the pixels identifies the presence (or absence) of a tracer particle/object. The 3D optical field—comprised of a plurality of the 2D cross-sectional slices stacked together—is in turn defined by a plurality of voxels (i.e., value representing an attribute, such as intensity, within three-dimensional space). A visual example of the numerical reconstruction is shown in FIG. 6*a*, in which the intensity of the voxels define the presence or absence of a particle (in this embodiment, dark or low intensity voxels represent particles, whereas light or high intensity voxels represent an absence of particles or background). In the embodiment shown in FIG. 6*a*, the z-axis represents the direction of the illumination (i.e., the longitudinal direction), wherein the plurality of 2D cross-sectional slices are defined in the xy plane and stacked in the direction of the z-axis. FIG. 6*a* illustrates one of the problems with reconstructing the position of particles based on 2D holograms, namely, a lack of resolution in the longitudinal direction (e.g., the z-direction). This shortcoming is addressed, in part, via the 3D deconvolution applied to the 3D optical field at step 86 (shown in FIG. 5).

Referring again to FIG. 5, the numerical reconstruction provided at step 84 requires determining a position of a particle based on the 2D hologram and in particular on the interference patterns, $I_h$, created by the interference of light scattered by the tracer particles with the unscattered portions of the coherent light source. The relationship between the 3D location of the particle and resulting interference pattern can be formulated as a convolution integral of the point spread function (PSF) of the imaging system and the 3D object. Hence, by treating the recorded hologram as a 2D aperture the 3D image of the object/objects (the 3-D complex optical field) can be reconstructed through:

$$u_p(x,y,z) = I_h(x,y) \otimes h(x,y,z) \qquad (1)$$

where $u_p$ is the reconstructed 3D optical field, x, y, and z are lateral and longitudinal locations respectively, $I_h(x, y)$ is the 2D interference pattern, $\otimes$ represents the convolution operator and h (x, y, z) is the point-spread function (PSF) introduced by diffraction. In one embodiment, the PSF is estimated using the Rayleigh-Sommerfield Kernel:

$$h(x, y, z) = \frac{1}{j\lambda\sqrt{x^2 + y^2 + z^2}} \exp\left[jk\left(\sqrt{x^2 + y^2 + z^2}\right)\right] \qquad (2)$$

where k is propagation vector and A is the wavelength of illumination beam. Hence, one of the inputs utilized at step 84 may include the wavelength λ of the light source or illumination beam. In order to accelerate the computation, the convolution integral may calculated as a simple multiplication in the Fourier domain using fast Fourier transform as below $$u_p(x,y,z) = F^{-1}\{F[I_h(x,y)] \times F[h(x,y,z)]\} \qquad (3)$$

where F[ ] represents the fast Fourier transform operator. In brief, through convolving the recorded hologram ($I_h(x,y)$) with the diffraction PSF (h(x,y,z)), the corresponding 3D optical field $u_p(x, y, z)$ including stack of longitudinal scans or slices is reconstructed. This optical field represents the 3D image of the corresponding particle field. However, as shown in FIG. 6a, the 3D optical field suffers from depth of focus (DOF) problems and noises associated with the cross-interference of adjacent objects and out-of-focus objects. In one embodiment, the present invention utilizes a 3D deconvolution at step 86 to improve on these deficiencies.

At step 86, a 3D deconvolution is applied to the 3D optical field generated at step 84. In short, deconvolution is a process used to reverse the effects of convolution resulting from interaction between the signals, in this case as a result of the scattering of light by the tracer particles. In the embodiment shown in FIG. 5, a 3D point spread function (PSF) is received as an input at step 86 and applied to the 3D optical field (i.e., the entire stack of 2D images) to deconvolve the 3D optical field. In particular, the 3D point spread function is selected to take into account the coherent nature of the light source used to create the 2D holographic image. The deconvolution scheme computes the deconvolved 3D optical field as follows:

$$u_{p'}(x, y, z) = F^{-1}\left\{ \frac{F[I_{PSF}(x, y, z)]^* \times F[I_p(x, y, z)]}{(F[I_{PSF}(x, y, z)] \times F[I_{PSF}(x, y, z)]^*) + \beta} \right\} \qquad (4)$$

where $I_{PSF}$ and $I_p$ represent the intensity distributions of PSF of the optical system and original reconstructed 3D optical field, respectively, $u_{p'}$ is the corresponding deconvolved field, and β is a small constant used to prevent probable divisions by zero. Value of β should be smaller than the magnitude of the other term in the denominator, and in one embodiment is selected as ~0.5 for a wide range of tested tracer particle holograms. The 3D PSF function of the optical system ($I_{PSF}$) is modeled, using Rayleigh-Sommerfield's diffraction, as a 3D reconstruction of a synthetic hologram generated for a one pixel size aperture located in the center of measurement volume. It is noteworthy that the 3D PSF function can be also obtained experimentally through reconstruction of a hologram of a point-like object. The output of the 3D deconvolution is a deconvolved 3D optical field, such as that shown in FIG. 6b. As compared with the original 3D optical field shown in FIG. 6a, the deconvolved 3D optical field shown in FIG. 6b illustrates an improved longitudinal resolution. In other embodiments, rather than an instant 3D deconvolution scheme an iterative scheme for 3D deconvolution may be utilized.

Steps 88, 90 and 92 describe segmenting/identifying particles within the deconvolved 3D optical field, as indicated by the dashed line. Typically, this process would involve users selecting—based on the application—thresholds to be applied to the 3D optical field in order to group and identify particles. As a result, this process was heavily reliant on user expertise. The embodiment shown in FIG. 5 instead utilizes a series of steps that allow the process of segmenting/identifying particles to be automated.

At step 88, 3D local signal-to-noise (SNR) enhancement is applied to the deconvolved 3D optical field to generate an enhanced 3D optical field. The purpose of the SNR enhancement is to equalize the intensity of the 3D optical field. In one embodiment, this includes first dividing the deconvolved optical field into object domain and background using a single threshold, and then performing local intensity normalization on the object domain. For example, the threshold for segmenting background, $I_{Thr0}$, may be automatically determined using 2D minimum intensity map of the optical field as follows:

$$I_{Thr0} = \text{Avg}(I_{min}) - \text{Avg}(I_\sigma) - \sigma(I_\sigma) \qquad (5)$$

where Avg( ) and σ( ) are average and standard deviation operators, $I_{min}$ and $I_\sigma$ represent the standard deviation and minimum intensity of pixels within an interrogation window which scans over the entire 2D minimum intensity map of the optical field, overlapping adjacent interrogation window scans by a determined amount (e.g., 50% overlap). In one embodiment, the size of interrogation window is selected to be four times the diameter of the tracer particles (e.g., $4 \times D_p$, wherein $D_p$ is the particle diameter). For example, the interrogation window may have a size of 8×8 pixels for embodiments in which the diameter of the tracer particles is approximately two pixels. The interrogation window of adjustable size can be further embedded to accommodate holograms recorded over a wide range of applications. The background is segmented by selecting those voxels having an intensity level above a threshold $I_{Thr0}$ (indicating a background pixel) and then assigning those voxels a maximum intensity of the 3D optical field to ensure subsequent identification of other voxels as background. The subsequent local intensity normalization is conducted through 3D min-max filtering over the object domain as below:

$$I'(x, y, z) = \frac{I(x, y, z) - \text{Min}(I_V)}{\text{Max}(I_V) - \text{Min}(I_V)} \quad (6)$$

Where I (x, y, z) and I' (x, y, z) are the original and the normalized intensity values of the voxel located at (x, y, z), respectively, and the Min( ) and Max( ) are the minimum and maximum calculation operators, respectively, and $I_V$ represents the intensity distribution within the corresponding interrogation block shifting over the entire object domain with a determined amount of overlap (e.g., 50%). In one embodiment, the size of the interrogation block is determined using the depth of field (DOF) estimate of particle objects through synthetic hologram simulation with similar magnification and based on the largest tracer used in the experiment. In one embodiment, the DOF is defined as the distance between the 75% intensity peaks around the particle centroids, and to account for the uncertainties present in the actual experiment, the synthetically calculated DOF is doubled as an estimate of DOF. The result is an enhanced 3D optical field.

At step 90, automatic 3D thresholding is applied to the enhanced 3D optical field to generate a partitioned 3D optical field. Application of 3D local SNR enhancement at step 88 allows a single threshold value to be applied to the entire measurement volume in order to identify and segment particles from the background. This is in contrast with systems that require the user to select the thresholds to be applied to the 3D optical field based on the user's experience. In one embodiment, the threshold value is automatically selected based on an intensity histogram of xy 2D minimum intensity map of the reconstructed 3D optical field. In part, because the local SNR enhancement provides a clear separation between the background and objects of interest (i.e., particles), the threshold value can be automatically calculated from the histogram of intensity values of the SNR enhanced minimum intensity map by finding the maximum intensity within the object domain.

Figure 6C:
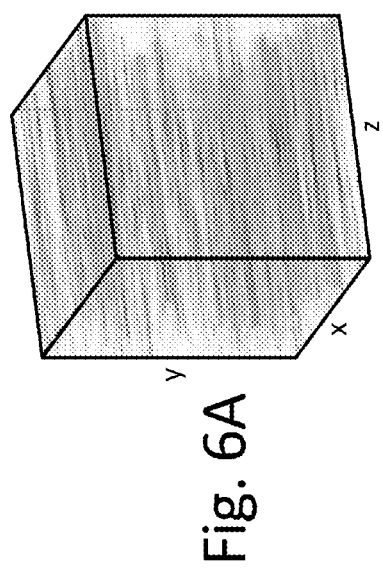
FIG. 6c illustrates the xy plane and xz plane minimum intensity map prior to 3D deconvolution.
Figure 6B:
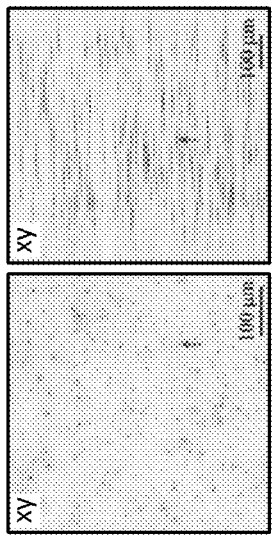
Figure 6D:
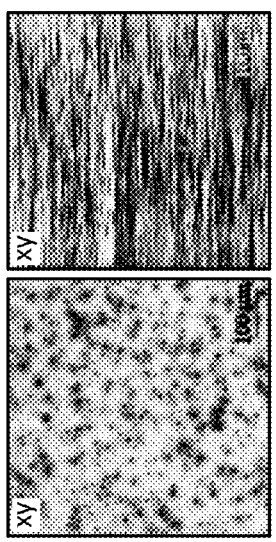
FIG. 6d illustrates the xy plane and xz plane minimum intensity map subsequent to 3D deconvolution according to an embodiment of the present invention.

At step 92, following automatic 3D thresholding of the optical field, 3D object segmentation includes joining the 2D segments into 3D objects through a merge operator to connect thresholded voxels located within a threshold distance from each other, an example of which is shown in FIG. 6*d*. In short, those voxels determined at step 90 to be directed to a particle are joined with adjacent or semi-adjacent voxels to form 3D objects representing particles. In one embodiment, the threshold distance used at step 92 is defined in relation to the particles being extracted (e.g., twice the diameter of the particle). To reduce false positives during particle segmentation, a subsequent size filter may be applied to eliminate objects too small to represent an actual particle. For example, particles extracted in DIH systems are characterized by some degree of longitudinal elongation, whereas "false" particles resulting from cross-interference or out-of-focus diffraction do not exhibit this longitudinal elongation (i.e., are shorter) and therefore can be filtered based on their shorter longitudinal length. In one embodiment, the filter utilized to eliminate false particles is based on the lowest depth of field (DOF) estimate for the particle field, such that any 3D objects having a longitudinal length less than the DOF estimate are filtered as not directed to "real" particles (i.e., particle-noise differentiation). The DOF estimate may be automatically calculated through a synthetic hologram simulation with similar magnification and for smallest tracer size used in the experiment.

Having filtered "false particles", particle centroids ($x_i$, $y_i$, $z_i$), diameters ($D_{pi}$) and in-focus cross sections $A_{pi}$ are finally calculated based on the determined geometric center of the remaining 3D objects (also referred to as centroids or blobs). A velocity vector field is calculated for any two consecutive holograms using their corresponding extracted centroid fields ($x_i$, $y_i$, $z_i$). In this way, objects identified as particles are identified and segmented, and information regarding the particles is identified including position of the particle and velocity of the particle, assuming the particle was successfully segmented in a previous hologram. Particle information is extracted and saved. However, not all particles are likely to be extracted. In particular, one drawback of the 3D deconvolution performed at step 86, is that the 3D deconvolution process may reduce the interference pattern of some particles within the field of view, in particular, those particles for which the 2D pattern is contaminated by cross-interference and for those particles located close to the borders of the reconstructed 3D optical field. An example of contamination by cross-interference is illustrated in FIG. 3B, in which the position of particles 62*a* and 62*b*' resulted in cross-contamination of 2D hologram fringe patterns 68*a* and 68*b*'. As a result, while improving longitudinal resolution, the 3D convolution may result in a decrease in particles extracted from the 2D hologram.

To combat these issues and increase the number of extracted particles, an inverse iterative particle extraction (IIPE) process is utilized as shown at step 94 (which includes steps 96 and 98). In general, the IIPE process takes those particles that were identified and extracted from a most recent iteration and acts to remove the influence of those particles from the 2D hologram. The updated 2D hologram, devoid of the interference patterns of those particles already extracted from the hologram, is then provided as feedback to steps 84-92 to remove another round of particles/objects. This process continues iteratively, with additional particles removed in each subsequent iteration. At the end of the process, the 2D hologram—initially littered with many interference patterns—may be relatively devoid of patterns, indicating that most particles have been extracted. A plurality of iterations may be employed in order to extract the desired concentration of particles.

In one embodiment, particle removal at step 96 operates by removing segmented particles from the 3D optical field. For example, extracted particles may be removed from the 3D optical field by filling the in-focus cross section of the segmented particle to be removed with the average complex value of the reconstructed optical field, which amounts to filling the cross-section of the segmented particle with an intensity level equivalent to that of the background. As a result, the previously segmented particle is essentially removed/erased from the 3D optical field. The updated optical field (with the signatures of the extracted particles removed) may be provided in feedback or may be utilized to generate an updated 2D hologram via forward scattering for the next iteration of particle segmentation/extraction. The updated 2D hologram is utilized at steps 84-92 to identify/segment additional particles, In one embodiment, the particle removal step shown at step 96 may utilizes an iterative process for removing segmented/extracted particles (or rather, the interference pattern generated by the extracted particles) from the 2D hologram (described in more detail with respect to FIG. 8*a*. Removing the segmented particles from the 2D hologram results in the generation of an updated 2D hologram that is provided in feedback to step 84 for the next round of particle identification/segmentation. In other embodiments, rather than remove particles from the 2D holograms, the effect or presence of the extracted particles may be removed from the 3D optical field, without updating the 2D hologram. In this embodiment, rather than the iteration returning to step 84 with an updated 2D hologram, feedback would be provided to step 86 in the form of an updated 3D optical field.

At step 98, a determination is made whether to end the iterative process or proceed with a subsequent iteration. In the embodiment shown in FIG. 5, the updated hologram (with the signatures of extracted particles removed) is compared or cross-correlated with the previous hologram. In this embodiment, the iteration ends when the calculated correlation exceeds a defined threshold (e.g., 0.99 or 99%), indicating that there are few additional particles that can be extracted from the updated hologram. If the calculated correlation does not exceed the defined threshold, then the process continues at step 84 with a subsequent iteration. In one experiment, five iterations were required to reach a cross-correlation threshold greater than 99%, with approximately 30% of the segmented/extracted particles being extracted after the first iteration. This demonstrates the benefit of the IIPE methodology, and also demonstrates the ability to leverage higher concentrations of tracer particles using the inverse iterative particle extraction process. In other embodiments, rather than rely on a cross-correlation threshold, a predetermined number of iterations may be relied upon to extract a sufficiently high percentage of particles.

FIGS. 6a and 6b are both visual representations of the 3D optical field created as a result of the numerical reconstruction performed at step 84 (shown in FIG. 5), wherein the 3D optical field shown in FIG. 6a is prior to 3D deconvolution and the 3D optical field shown in FIG. 6b illustrates the effect of the 3D deconvolution performed at step 86. In particular, FIG. 6a illustrates some of the shortcomings associated with the 3D optical field prior to 3D deconvolution, namely out-of-focus distortion and poor longitudinal resolution. FIG. 6b illustrates how both of these issues are improved following the 3D deconvolution. In particular, FIG. 6b illustrates the improvement in longitudinal resolution of the 3D optical field following 3D deconvolution.

Figure 6E:
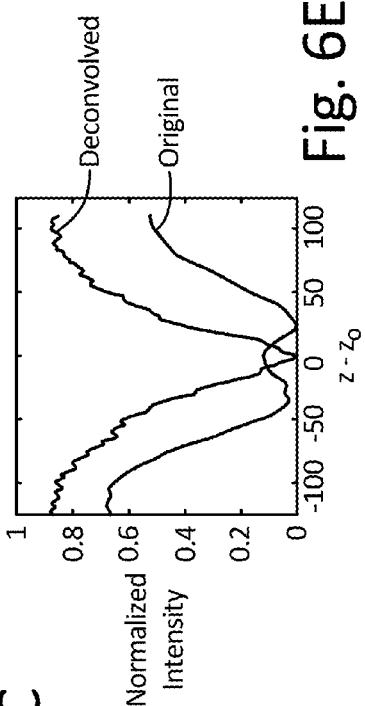
FIG. 6e is a normalized intensity graph that illustrates the longitudinal resolution of particles in the original 31) optical image and in the deconvolved 3D optical image according to an embodiment of the present invention.

FIG. 6c illustrates in additional detail the out-of-focus distortion and poor longitudinal resolution associated with the 3D optical image. The image on the left illustrates the xy plane minimum intensity map, and in particular illustrates the out-of-focus distortion associated with particles (dark spots) in the xy plane. The image on the right illustrates the xz plane minimum intensity map (i.e., longitudinal direction) and in particular illustrates the lack of longitudinal resolution in the xz plane. When compared with FIG. 6d, which illustrates the xy and xz plane minimum intensity map following the 3D convolution, there is evident improvement in both the out-of-focus distortion as illustrated in the xy plane (left-side image) and in the longitudinal resolution illustrated in the xz plane (right-side image). FIG. 6e is a normalized intensity graph that illustrates the longitudinal resolution of particles in the original 3D optical image (line 100) and in the deconvolved 3D optical image (line 102). As apparent from the normalized intensity graph, the deconvolved 3D optical image provides improved longitudinal resolution.

FIGS. 7a-7c illustrate the effect of applying the 3D local SNR enhancement (e.g., per step 88 as shown in FIG. 5). In particular, FIG. 7a illustrates the xy and xz minimum intensity maps of the 3D optical field following the deconvolution (i.e., same minimum intensity maps shown in FIG. 6d), while FIG. 7b illustrates the xy and xz minimum intensity maps of the 3D optical field following 3D local SNR enhancement. As indicated by comparison of FIGS. 7a and 7b, the uniformity of particle intensity is improved and the background noise is suppressed significantly after application of 3D SNR enhancement. FIG. 7c illustrates a normalized number of pixels charted against gray-scale intensity both before 3D local SNR enhancement (shaded region 104) and after 3D local SNR enhancement (shaded region 106). In particular, FIG. 7c illustrates the clear separation between the background and objects/particles, with objects/particles represented by pixels of lower intensity and the background is represented by pixels of higher intensity (e.g., approximately 255). As illustrated in FIG. 7c, before SNR enhancement, the grouping of normalized number of pixels 104 indicates a large number of pixels in the 100 to 250 range, which does not identify them as clearly objects/particles or background. After SNR enhancement, the grouping of normalized number of pixels 106 indicates an increase in particles located in the 0 to 150 range (i.e., more clearly identified as objects/particles), with another large grouping occurring at exactly 250, indicating a clear delineation between objects/particles and background.

Figure 8A:
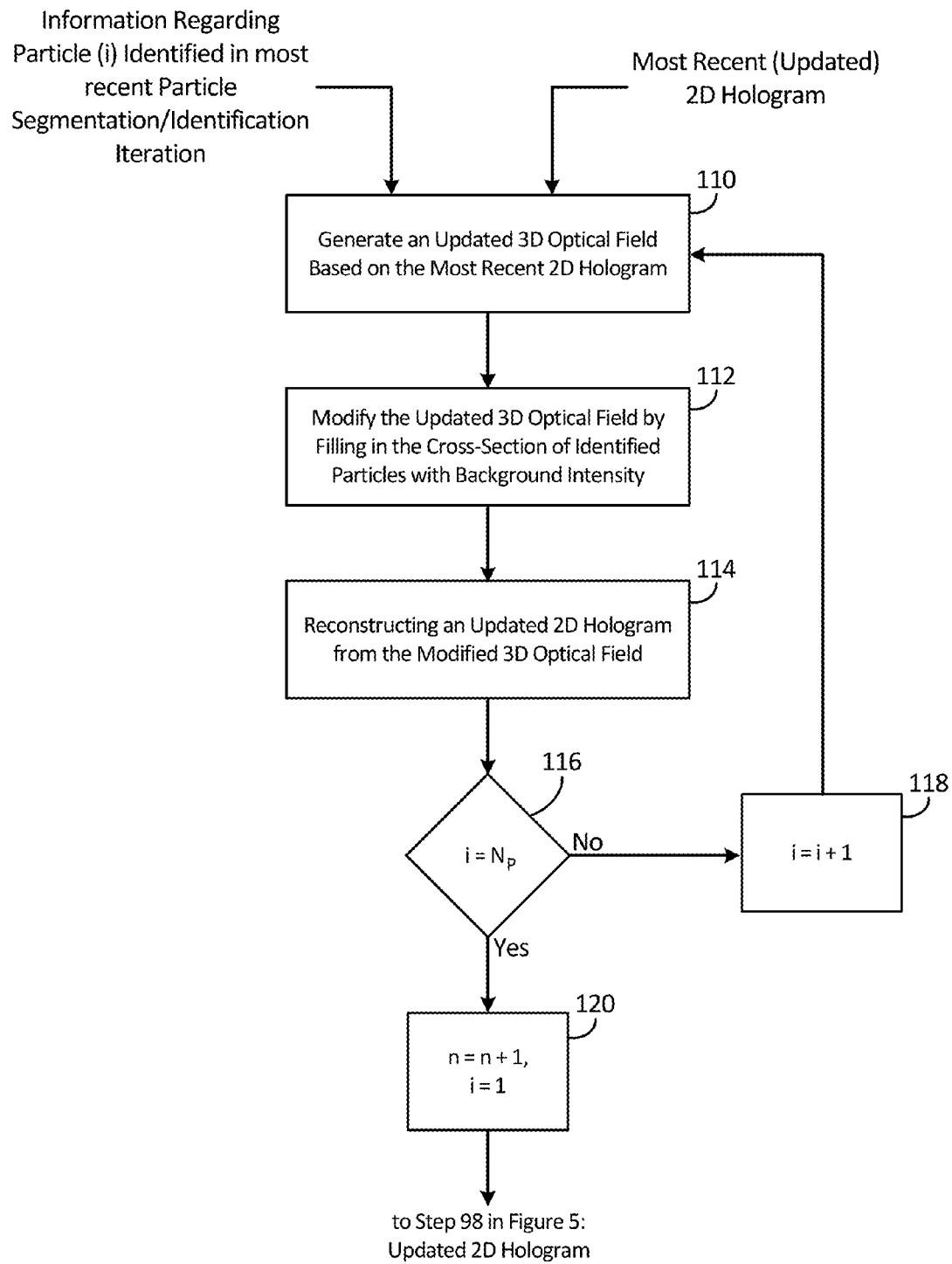
FIG. 8a is a flowchart that illustrates in additional detail a portion of the inverse iterative particle extraction method that is responsible for removing extracted particles from the 2D hologram according to an embodiment of the present invention.
Figure 8B:
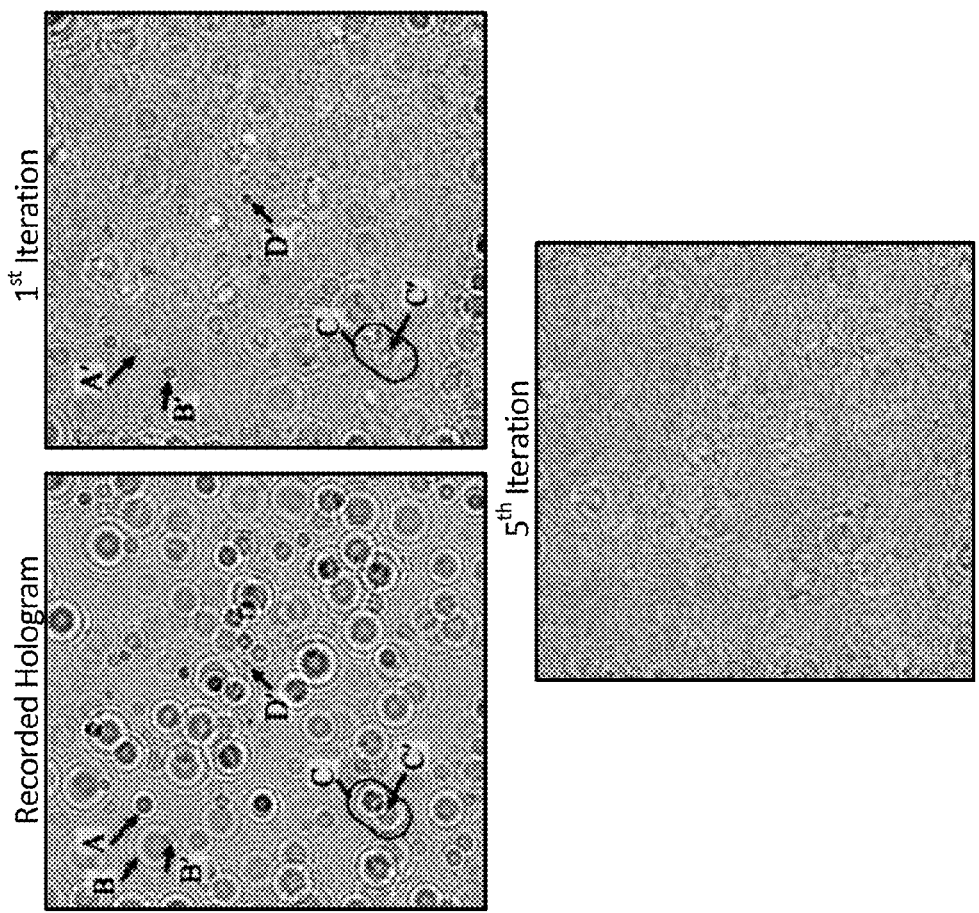
FIG. 8b illustrates the effects of the inverse iterative particle extraction (IIPE) technique on the 2D holograms through various numbers of iterations according to an embodiment of the present invention.
Figure 8C:
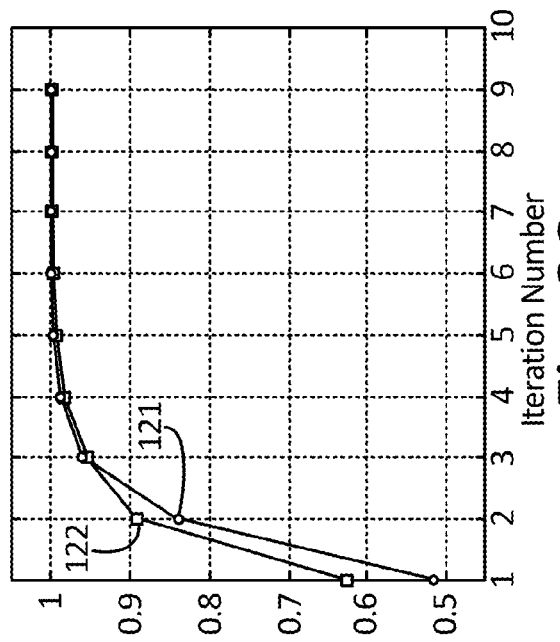
FIG. 8c is a graph that illustrates how the concentration of particles affects the particles extracted in each iteration and the number of iterations required for each according to embodiments of the present invention.

FIG. 8a is a flowchart that illustrates in additional detail a portion of the inverse iterative particle extraction method that is responsible for removing extracted particles from the 2D hologram according to an embodiment of the present invention. FIG. 8b illustrates how the 2D hologram changes with each subsequent iteration and removal of extracted particles, and FIG. 8c illustrates the cross-correlation coefficient calculated at each iteration for different concentrations of particles.

In general, FIG. 8a describes how each extracted particle (i.e., those particles identified within the 3D optical field at step 92 as shown in FIG. 5) is removed from the reconstructed optical field by filling the cross section of the removed particle with an intensity equivalent to that of the background, and then using the updated 3D optical field to generate an updated 2D hologram, wherein the updated hologram should reflect the removal of particles from the 3D optical field.

More particularly, extracted particles are removed from the reconstructed optical field by filling its in-focus cross section with the average complex value of the reconstructed optical field (background). The updated optical field (with extracted particles signature removed) is then used to generate the updated hologram through backward diffraction for the next round of particle extraction. This iterative process can be formulated in following steps:

$$u_p(x,y,z_i)_n = I'_{h|n}(x,y) \otimes h(x,y,z_i) \qquad \text{Eq. 7}$$

$$u_p(A_{pi}(x_i,y_i),z_i)_n = \text{Avg}(u_p(x,y,z_i)_n) \qquad \text{Eq. 8}$$

$$I'_{h|n}(x,y) = |u_p(x,y,z_i)_n \otimes h(x,y,-z_i)|^2 \qquad \text{Eq. 9}$$

where i represents the particle ID number ranging from 1 to $N_p$ (the total number of segmented or extracted particles at removal iteration n), $A_{pi}$ is the in-focus cross section of particle i (calculated in the 3D object segmentation step), and I'h|n and $u_p(x,y,z_i)_n$ represent the particle removed hologram and the corresponding particle-removed optical field after n iterations, respectively. Note that the order of removal of the particles does not matter, and each iteration ends when all the detected particles from the previous iteration are removed, i.e. i=$N_p$.

With respect to the embodiment shown in FIG. 8a, inputs to the process (shown at the top of FIG. 8a) include the most recent reconstruction of the 2D hologram I'h|n(x,y) and information regarding the particle(s) i identified in the most recent iteration whose influence needs to be removed from the 2D hologram, wherein information includes the in focus cross-section/position $A_{pi}(x_i, y_i)$, $z_i$ of the particle i being extracted/removed from the image. At step 110 an updated 3D optical field $u_p(x,y,z_i)_n$ is generated based on the most recent 2D hologram I'hIn via convolution with the point spread function $h(x, y, z_i)$—for example as indicated by Eq. 7 above. At step 112, the 3D optical field is modified by filling in the cross-section of particle being extracted $A_{pi}(x_i, y_i)$, $z_i$ with a background intensity via the average pixel intensity $Avg(u_p(x, y, z_i)_n)$—for example as indicated by Eq. 8 above. In this way, the particle i is effectively erased from the 3D optical field $u_p(x,y,z_i)_n$. At step 114, the 2D hologram I'hIn(x,y) is reconstructed from the updated 3D optical field such that the updated 2D hologram reflects removal of particle i—for example as shown in Eq. 9 above.

At step 116, a determination is made whether the most recently removed particle represented the last particle to be removed from the 2D hologram (i.e., does $i=N_p$, wherein $N_p$ represents the total number of particles extracted from the 3D optical field in the latest iteration, and thus the number of particles that must be removed from the 2D hologram). If i does not equal $N_p$, then the value of i is incremented by one at step 118 and particle removal proceeds at step 110 to remove the influence of the next particle from the 2D hologram. If i does equal $N_p$, indicating that the last particle identified/segmented in the 3D optical field (at step 92, shown in FIG. 5) has also been removed from the 2D hologram, then the value of n is incremented (i.e., n=n+1), the value of i is reset to one (1) to prepare for a subsequent iteration of the IIPE. With respect to the embodiment shown in FIG. 5, the updated 2D hologram may be compared to a previous iteration of the 2D hologram to determine whether another iteration of particle extraction is required. In other embodiments, the number of iterations n completed is utilized in isolation to determine whether to end the process. If another round of particle identification/segmentation is required, then steps 84-92 are performed once again—as shown in FIG. 5—to identify/segment additional particles based on the updated 2D hologram that removes theh presence/influence of previously identified/extracted particles. The variable i representing which particle is currently being removed from the 2D hologram is reset to 1 to prepare for a next iteration of particle removal from a 2D hologram—if required.

The embodiment shown in FIG. 8a reflects one method of removing the influence of identified/segmented particles from the 2D hologram. In the embodiment shown in FIG. 8a, the 2D hologram (updated with each iteration of steps 110-116) is utilized to generate a 3D optical field, wherein the particle to be extracted/removed is removed from the 3D optical field, followed by reconstruction of the 2D hologram from the updated 3D optical field. In other embodiments, all particles $N_p$ may be removed from the 3D optical field without reconstructing the updated 2D hologram for each iteration of particle removal. In this way, generation of the updated 3D optical field (at step 110) and the reconstruction of an updated 2D hologram (at step 114) is only done once for each iteration of identified particles, rather than once each time for each identified particle (as shown in FIG. 8a).

FIG. 8b illustrates the effects of the inverse iterative particle extraction (IIPE) technique on the 2D holograms through various numbers of iterations. The top left image represents an initially recorded 2D hologram prior to removal of any particles. During the first iteration, steps 82-92 would be performed to identify and segment a first plurality of particles. A first plurality of these particles, labeled A, B and C, are shown in the upper-left hand image, although it should be understood that a plurality of additional particles beyond those labeled would also be extracted. At step 96 (as shown in FIG. 5), these particles are removed from the 2D hologram. In one embodiment, steps 110-116 (shown in FIG. 8a) are performed to iteratively remove these particles from the 2D hologram. Particles B', C', and D' are highlighted in the upper-left hand image, but were not segmented as part of the initial particle removal. Highlighting of these particles shows how subsequent iterations identify and segment these particles that are at least partially obscured in the initial iteration. The upper-right hand image illustrates the 2D hologram (i.e., first iteration 2D hologram) following removal of particles A, B, and C (along with a number of other particles, not labeled) from the initial 2D hologram. In this iteration, particles A', B', C', and D' are identified and segmented at steps 84-92, and therefore these particles must be removed from the 2D hologram at step 96 (e.g., steps 110-116 shown in FIG. 8a). The lower image illustrates the 2D hologram after a fifth iteration. As compared with the initially recorded 2D hologram and the first iteration of the 2D hologram, the 2D hologram shown with respect to the fifth iteration has significantly fewer interference patterns associated with particles. As particles are removed from each 2D hologram in consecutive iterations, the cross-correlation between consecutive 2D holograms increases as fewer and fewer differences exist between each consecutive 2D hologram. The effect on cross-correlation is illustrated in FIG. 8c, which illustrates how the cross-correlation coefficient increases toward a value of one with each consecutive iteration. The cross-correlation coefficient approaching a value of one indicates that very few particles are being removed from each 2D hologram, and therefore very few differences are identified between consecutive 2D holograms.

In addition to showing how the cross-correlation coefficient increases with each subsequent iteration, the graph shown in FIG. 8c also highlights how the concentration of particles affects the particles extracted in each iteration and the number of iterations required for each. In particular, line 120 illustrates a particle density of 1800 p/mm$^3$, while line 122 illustrates a particle density of 3000 p/mm$^3$. In the embodiment shown in FIG. 8c, both lines converge toward one another after the $3^{rd}$ iteration, and by the $5^{th}$ iteration indicate that very few additional particles are being extracted with each subsequent iteration. The embodiment shown in FIG. 8 indicates that five iterations provide sufficiently good results that additional iterations are not needed. Therefore, in some embodiments, rather than use a cross-correlation metric to determine when to end the inverse iterative particle extraction (IIPE) process, a predetermined number of iterations may be utilized (e.g., five). In this case, there would be no need to calculate the cross-correlation metric or compare the calculated cross-correlation metric to a threshold as shown at step 98 (FIG. 5).

FIGS. 9a and 9b are graphs that illustrate the results of an implementation of the DIH-PIV method according to an embodiment of the present invention. Various experimental parameters were modified, with the results shown for each. Experimental parameters include volume depth ($L_z$), particle concentration ($C_p$) and particle size ($D_p$). The results shown in FIGS. 9a and 9b illustrate application of the analysis shown in FIG. 5 on a set of synthetic holograms generated using Rayleigh-Sommerfield diffraction. The synthetic holograms include randomly distributed monodispersed tracer particles with a particle concentration $C_p$ ranging from 1600-4800 particles/mm$^3$. In addition, different tracer particle diameters $D_p$ were modeled, ranging in size from 3 μm to 6 μm and having a volume depth 4 that ranges from 0.5 to 1 mm. Following completion of the algorithm, the results are compared to the tracer particles included to create the synthetic hologram to determine the extraction rate ($E_p$) and position error (δ), wherein the extraction rate is calculated for each hologram as the ratio of accurately extracted particles (i.e., the particles extracted with positioning errors of δ≤2×$D_p$ to the total number of particles included in the synthetic hologram). The position error is defined for each hologram as the maximum positioning error for individual particles which 95% of the particles lie within −δ to δ.

FIG. 9a compares the extraction rate $E_p$ of particles under various circumstances, with particle concentrations ranging from 1600 particles/mm$^3$ to 4800 particles/mm$^3$. Line 130 illustrates a volume depth $L_z$ of 0.512 mm and a particle size $D_p$ of 3 μm. Line 132 illustrates a volume depth $L_z$ of 0.512 mm and a particle size $D_p$ of 6 μm. Line 134 illustrates a volume depth 4 of 1.024 mm and a particle size $D_p$ of 3 μm. Finally, line 136 illustrates a prior art, non-iterative particle extraction of particles having a particle size $D_p$ of 3 μm and a volume depth $L_z$ of 0.512 mm. The results indicates that the inverse iterative particle extraction (IIPE) methodology applied according to an embodiment of the present invention provides an improved extraction rate $E_p$ as compared with the non-iterative approach. In particular, while the extraction rate remains relatively stable as the particle concentration increase (along the x-axis), the non-iterative approach shows a decrease of approximately 60% in extraction rate $E_r$ as the particle concentration increases to 4800 particles/mm$^3$. In contrast, the extraction rate stayed above 97% for the embodiment in which the volume depth $L_z$ is 0.512 mm and the particle size $D_p$ is 3 μm.

FIG. 9b illustrates the positioning error (δ) of the particles extracted by the IIPE methodology at various particle concentrations and at various parameters of particle size and volume depth. Once again, the present invention illustrates the effectiveness of the IIPE methodology even as the concentration of particles increases. Line 140 illustrates a volume depth $L_z$ of 0.512 mm and a particle size $D_p$ of 3 μm. Line 142 illustrates a volume depth $L_z$ of 0.512 mm and a particle size $D_p$ of 6 μm. Line 144 illustrates a volume depth $L_z$ of 1.024 mm and a particle size $D_p$ of 3 μm. In general, the results of FIG. 9b illustrates that the positioning error δ remains relatively constant despite increasing particle concentrations and despite changes to the volume depth $L_z$ and particle size $D_p$.

In this way, the present disclosure describes a system and method of utilizing digital inline holography (DIH) to image objects, and in particular how DIH systems can be utilized in particle image velocimetry (PIV) applications. Benefits of the DIH system is the relatively inexpensive costs, including a single light source (e.g., laser) and single imaging device. This is in contrast with many applications in which 3D imaging requires multiple cameras coordinated with one another to image particles in a 3D viewing volume. In addition to the relatively inexpensive hardware requirements for DIH-PIV applications, the present disclosure provides a number of steps to analyze and enhance the 2D hologram captured as part of the DIH system. In particular, the present disclosure takes advantage of an inverse iterative particle extraction (IIPE) process, wherein those particles identified and extracted from the 2D hologram are removed from the 2D hologram. That is, the presence of the particles on the 2D hologram is removed, so that a subsequent iteration of the particle extraction algorithm is able to extract additional particles not previously visible or easily extracted in a first iteration. In this way, the present disclosure is able to successfully identify/extract a higher percentage of particles located in a viewing volume, and at higher particle concentration levels. In addition, the present disclosure may find applicability in areas other than PIV, and even in more advanced PIV applications. For example, in one application, in addition to merely monitoring position/velocity of particles, the vorticity of the particles may also be monitored. In one embodiment, a marker or plurality of markers are included in each tracer particle, wherein the marker is substantially smaller than the size of the particle. The DIH-PIV system may be utilized to monitor not only the tracer particles for velocity information, but may also monitor the marker or markers included in each tracer to detect vorticity.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of extracting particles from a two-dimensional (2D) hologram recorded as part of a digital inline holography system, the method comprising:
   a. reconstructing a three-dimensional (3D) optical field from the recorded 2D hologram;
   b. segmenting particles from the reconstructed 3D optical field, wherein segmented particles are identified by particle location in three-dimensional space and a cross-sectional area of the segmented particle; and
   c. computationally removing the segmented particles from the 2D hologram to generate an updated 2D hologram; and
   repeating steps (a)-(c) until a threshold is met.

2. The method of claim 1, further including:
   applying signal-to-noise (SNR) enhancement to the recorded 2D hologram, wherein the 3D optical field is reconstructed from the enhanced 2D hologram.

3. The method of claim 1, further including:
   applying a 3D deconvolution to the reconstructed 3D optical field to generate a deconvolved 3D optical field that is provided to step (b).

4. The method of claim 1, wherein segmenting particles from the 3D optical field includes:
   applying a local 3D signal-to-noise (SNR) enhancement of the 3D optical field to equalize the intensity of the 3D optical field;
   selecting an automatic 3D thresholding based on an intensity histogram of an xy 2D minimum intensity map of the reconstructed 3D optical field;
   applying the selected automatic 3D threshold to the enhanced 3D optical field to distinguish voxels representative of particles from background voxels; and
   joining the 2D segments into 3D objects through a merge operator to connect voxels located within a threshold distance from one another, wherein merged voxels represent a segmented particle.

5. The method of claim 4, wherein segmenting particles from the reconstructed 3D optical field further includes calculating particle centroids, diameters, and in-focus cross sections of the segmented particles.

6. The method of claim 1, wherein computationally removing the segmented particles from the 2D hologram includes:
generating an updated 3D optical field based on the updated 2D hologram;
modifying the updated 3D optical field by filling in the cross-sectional areas of segmented particles with intensity values equal to background values; and
reconstructing an updated 2D hologram from the modified 3D optical field.

7. The method of claim 1, wherein computationally removing the segmented particles from the 2D hologram includes:
(d) generating an updated 3D optical field based on the updated 2D hologram;
(e) modifying the updated 3D optical field by filling in the cross-sectional area of one of the segmented particles with intensity values equal to background values;
(f) reconstructing an updated 2D hologram from the modified 3D optical field; and
repeating steps (d)-(f) until all segmented particles have been removed from the 2D hologram.

8. The method of claim 1, wherein the threshold utilized is based on a comparison of the updated hologram with a previous hologram to determine correlation, wherein when correlation between the updated hologram and the previous hologram exceeds a threshold value.

9. A digital inline holography particle image velocimetry (DIH-PIV) system comprising:
a holographic recording system configured to record two-dimensional (2D) holograms in response to interaction of planar wave fronts with a plurality of particles located in a particle field;
a processing system that receives the recorded 2D holograms and processes the 2D holograms to identify particle locations within the particle field, wherein the processing system (a) reconstructs a three-dimensional (3D) optical field from the recorded 2D hologram, (b) segments particles from the reconstructed 3D optical field, wherein segmented particles are identified by particle location in three-dimensional space and a cross-sectional area of the segmented particle, and (c) computationally removes the segmented particles from the 2D hologram to generate an updated 2D hologram, wherein the steps (a)-(c) are repeated until a threshold is met.

10. The DIH-PIV system of claim 9, wherein the processing system applies a signal-to-noise (SNR) enhancement to the recorded 2D hologram, wherein the 3D optical field is reconstructed from the enhanced 2D hologram.

11. The DIH-PIV system of claim 9, wherein the processing system applies a 3D deconvolution to the reconstructed 3D optical field to generate a deconvolved 3D optical field that is utilized by the processing system to segment particles.

12. The DIH-PIV system of claim 9, wherein the processing system segments particles from the reconstructed 3D optical field by applying a local 3D signal-to-noise (SNR) enhancement of the 3D optical field to equalize the intensity of the 3D optical field, selects an automatic 3D thresholding based on an intensity histogram of an xy 2D minimum intensity map of the reconstructed 3D optical field, applies the selected automatic 3D threshold to the enhanced 3D optical field to distinguish voxels representative of particles from background voxels; and joins the 2D segments into 3D objects through a merge operator to connect voxels located within a threshold distance from one another, wherein merged voxels represent a segmented particle.

13. The DIH-PIV system of claim 12, wherein the processing system calculates particle centroids, diameter, and in-focus cross-sections for each segmented particle.

14. The DIH-PIV system of claim 9, wherein the processing system computationally removes the segmented particles from the 2D hologram by generating an updated 3D optical field based on the updated 2D hologram, modifying the updated 3D optical field by filling in the cross-sectional areas of segmented particles with intensity values equal to background values, and reconstructing an updated 2D hologram from the modified 3D optical field.

15. The DIH-PIV system of claim 9, wherein the processing system computationally removes the segmented particles from the 2D hologram by (d) generating an updated 3D optical field based on the updated 2D hologram, (e) modifying the updated 3D optical field by filling in the cross-sectional area of one of the segmented particles with intensity values equal to background values, and (f) reconstructing an updated 2D hologram from the modified 3D optical field, wherein the processing system repeats steps (d)-(f) until all segmented particles have been removed from the 2D hologram.

16. The DIH-PIV system of claim 9, wherein the threshold utilized is a set number of iterations.

17. The DIH-PIV system of claim 9, wherein the threshold utilized is based on a comparison of the updated hologram with a previous hologram to determine correlation, wherein when correlation between the updated hologram and the previous hologram exceeds a threshold value.

18. The DIH-PIV system of claim 9, wherein the holographic recording system comprises:
a light source
one or more optical devices configured to direct the planar wave front into the particle field that includes the plurality of particles; and
a camera configured to capture a 2D hologram resulting from the interaction of the planar wave front with the plurality of particles.

19. A computer-readable storage medium having data stored therein representing software executable by one or more processors located in a computer system, wherein execution of the software by the one or more processors causes the computer system to identify particles within a recorded 2D hologram by performing a method comprising:
a. reconstructing a three-dimensional (3D) optical field from the recorded 2D hologram;
b. segmenting particles from the reconstructed 3D optical field, wherein segmented particles are identified by particle location in three-dimensional space and a cross-sectional area of the segmented particle; and
c. computationally removing the segmented particles from the 2D hologram to generate an updated 2D hologram; and
repeating steps (a)-(c) until a threshold is met.

20. The computer-readable storage medium of claim 19, the method further including:
applying signal-to-noise (SNR) enhancement to the recorded 2D hologram, wherein the 3D optical field is reconstructed from the enhanced 2D hologram.

21. The computer-readable storage medium of claim 19, the method further including:
applying a 3D deconvolution to the reconstructed 3D optical field to generate a deconvolved 3D optical field that is provided to step (b).

22. The computer-readable storage medium of claim 19, wherein segmenting particles from the 3D optical field includes:
- applying a local 3D signal-to-noise (SNR) enhancement of the 3D optical field to equalize the intensity of the 3D optical field;
- selecting an automatic 3D thresholding based on an intensity histogram of an xy 2D minimum intensity map of the reconstructed 3D optical field;
- applying the selected automatic 3D threshold to the enhanced 3D optical field to distinguish voxels representative of particles from background voxels; and
- joining the 2D segments into 3D objects through a merge operator to connect voxels located within a threshold distance from one another, wherein merged voxels represent a segmented particle.

23. The computer-readable storage medium of claim 22, wherein segmenting particles from the reconstructed 3D optical field further includes calculating particle centroids, diameters, and in-focus cross sections of the segmented particles.

24. The computer-readable storage medium of claim 19, wherein computationally removing the segmented particles from the 2D hologram includes:
- generating an updated 3D optical field based on the updated 2D hologram;
- modifying the updated 3D optical field by filling in the cross-sectional areas of segmented particles with intensity values equal to background values; and
- reconstructing an updated 2D hologram from the modified 3D optical field.

25. The computer-readable storage medium of claim 19, wherein computationally removing the segmented particles from the 2D hologram includes:
- (d) generating an updated 3D optical field based on the updated 2D hologram;
- (e) modifying the updated 3D optical field by filling in the cross-sectional area of one of the segmented particles with intensity values equal to background values;
- (f) reconstructing an updated 2D hologram from the modified 3D optical field; and
- repeating steps (d)-(f) until all segmented particles have been removed from the 2D hologram.

26. The method of claim 1, wherein the threshold utilized is a set number of iterations.

* * * * *